(12) United States Patent
Redner

(10) Patent No.: US 6,985,231 B2
(45) Date of Patent: Jan. 10, 2006

(54) METHOD AND APPARATUS FOR MEASURING THE OPTICAL QUALITY OF A REFLECTIVE SURFACE

(75) Inventor: Alex S. Redner, Plymouth Meeting, PA (US)

(73) Assignee: Strainoptics, Inc., North Wales, PA (US)

( * ) Notice: Subject to any disclaimer, the term of this patent is extended or adjusted under 35 U.S.C. 154(b) by 181 days.

(21) Appl. No.: 10/251,378

(22) Filed: Sep. 20, 2002

(65) Prior Publication Data
US 2003/0053066 A1   Mar. 20, 2003

Related U.S. Application Data

(60) Provisional application No. 60/323,539, filed on Sep. 20, 2001.

(51) Int. Cl.
  *G01N 21/55* (2006.01)
(52) U.S. Cl. ........................... 356/445; 356/448
(58) Field of Classification Search .............. 356/445, 356/446, 73, 600, 405, 406, 413, 425
  See application file for complete search history.

(56) References Cited

U.S. PATENT DOCUMENTS

| | | | |
|---|---|---|---|
| 3,788,750 A | 1/1974 | Maltby, Jr. et al. | ......... 356/239 |
| 3,857,637 A | 12/1974 | Obenreder | ................... 256/120 |
| 4,585,343 A | 4/1986 | Schave et al. | ............... 356/237 |
| 5,122,672 A | 6/1992 | Mansour | ...................... 250/571 |
| 5,128,550 A | 7/1992 | Erbeck | ........................ 250/572 |
| 5,210,592 A | 5/1993 | Bretschneider | ............. 356/371 |
| 5,251,010 A | 10/1993 | Maltby, Jr. | ................... 356/371 |
| 5,923,434 A * | 7/1999 | Lex | ............................ 356/445 |
| 5,926,262 A * | 7/1999 | Jung et al. | .................... 356/73 |
| 6,100,990 A | 8/2000 | Ladewski | .................... 356/445 |
| 6,111,653 A * | 8/2000 | Bucknell et al. | ............ 356/446 |
| 6,584,217 B1 * | 6/2003 | Lawless et al. | ............. 382/133 |

OTHER PUBLICATIONS

Moire Distortiometry for the Quantitative Evaluation of Optical Quality of Glass By. A. S. Redner & G. K. Bhat, Strainoptic Technologies, Inc. Glass Processing Days, Jun. 13-16, 1999, pp. 166-168.

* cited by examiner

*Primary Examiner*—Layla G. Lauchman
(74) *Attorney, Agent, or Firm*—Synnestvedt & Lechner LLP

(57) ABSTRACT

A method and apparatus for inspecting the optical quality of a reflective surface providing for the reflecting of a beam of light off the reflective surface, measuring an intensity of the reflected light at a first distance from said reflective surface, measuring an intensity of the reflected light at a second distance from said reflective surface, and comparing the intensity of the light measured at the two distances to determine the distortion of the reflective surface.

22 Claims, 7 Drawing Sheets

METHOD AND APPARATUS FOR MEASURING THE OPTICAL QUALITY OF A REFLECTIVE SURFACE

CROSS REFERENCE TO RELATED APPLICATION

This application claims the benefit of U.S. Provisional Application No. 60/323,539 filed Sep. 20, 2001, which is hereby incorporated by reference.

BACKGROUND

1. Field of the Invention

The present invention relates to a method and apparatus for measuring the optical quality of a reflective surface, for example, measuring the flatness of a sheet of glass that could contain a defective region where the surface is slightly curved.

2. Background and Technical Field of the Invention

Production of tempered glass consists of heating the material to its softening temperature, then fast chilling, to introduce compressive surface stresses and increase its strength. In this process, the hot material is supported and moved in and out of the heating chamber by a set of rolls. As result of the combined actions of sag between the rolls and roller eccentricity, the glass sheet deforms slightly, acquiring a surface waviness, also called Roller Wave, as shown in FIG. 1. When installed in a building, glass exhibiting this waviness will generate distortion of reflected images and be considered defective.

Several tools and methods are presently used to inspect tempered glass. With reference to FIG. 1 showing a sheet of glass 10 having a waviness, the simplest measuring tools include a depth gage revealing the depth w of the wave as a difference between peak 12 and valley 13 heights of the glass 10. The depth w of the wave, however, does not fully describe the optical distortion.

Other methods use optical means to quantify the optical distortion. With reference to FIG. 1A, devices such as that in U.S. Pat. No. 3,857,637 to Obenreder measures an angle B of a reflected beam of light 16 off of the surface 18 of the glass 10 using a beam-position sensing device 20. The reflected beam comes from a light source LS providing a beam of light 14 directed at the surface 18. This approach requires measuring the angle B of reflection at two or more points 22a, 22b, and recording the variation of the reflected angle B and the distance d between the measured points 22a, 22b, to permit the calculation of the optical distortion.

U.S. Pat. No. 5,251,010 to Maltby discloses a method that eliminates the need of measuring the distances d such as that illustrated in FIG. 1B. Maltby discloses methods whereby two parallel beams of light, which can be split from a single light source LS with partial mirrors 23 as shown, separated by a known distance d, are reflected off the inspected surface 18 and sensed by two position-sensing devices 20a, 20b. As result of the curvature due to the roller wave, these two beams 16a, 16b diverge or converge, and the change in the angle B between these beams provides the measure of the distortion.

A nearly identical device is described in U.S. Pat. No. 5,122,672 to Mansour and U.S. Pat. No. 5,210,592 to Betschneider. The two-beam approach requires very accurate beam-position detectors and does not account for the difficulties in measuring the beam position when the beam shape becomes irregular as result of the surface curvature. Another approach, described in Redner & Bhat, "New Distortion Measuring Method Using Digital Analysis of Projection-Moiré Patterns" SAE Transactions, 106 (6) 1997, uses the image of a Moiréscreen projected on a master, forming Moire fringes that reveal changes in magnification due to local curvature of the inspected item. The application of this method is also described in U.S. Pat. No. 5,128,550 to Erbeck. Another method based on measurements of the dimensional size of the reflected beam is described in U.S. Pat. No. 4,585,343 to Schave. In this method, edges of the reflected beam are located using an array of detectors. This method is essentially equivalent in performance to the two-beam method in U.S. Pat. No. 5,251,010 discussed above since the distance between the two edges of the reflected beam is used to measure angular changes. More recently, an approach proposed in U.S. Pat. No. 6,100,990 to Ladewski uses reflected images of gray-scale patterns. Assuming that the roller wave is periodic in nature, the distribution of light intensity analysis permits calculation of the optical power of the inspected surface.

All of the above methods have serious limitations, conceptual or practical in nature. Common difficulties include the following:

a) The measured angular deviation B is very small, and the detection of small changes in the reflected beam position cannot be accomplished accurately considering that the glass sheet vibrates as it emerges from the tempering furnace, and b) The surface curvature deforms the beam of light, making it difficult to locate its center using a position-sensing device.

For at least these reasons, a new method and apparatus that overcomes the limitations of the prior methods and apparatuses is desirable.

One objective of the invention is to provide for measuring optical distortion more accurately, eliminating the reflected beams position-sensing detectors used in the above described devices. Additional objects, advantages and novel features of the invention will be set forth in part in the description which follows, and in part will become apparent to those skilled in the art upon examination of the following or may be learned by practice of the invention.

SUMMARY OF THE INVENTION

The present invention provides a method for inspecting the optical quality of a reflective surface, such as flat sheet of glass. The method can include the following steps: (a) reflecting a beam of light off of the reflective surface; (b) measuring an intensity of the reflected light at a first distance from said reflective surface; (c) measuring an intensity of the reflected light at a second distance from said reflective surface, where the first distance is different than said second distance; and (d) comparing the light intensity measured in paragraph b with the light intensity measured in paragraph c to determine the distortion of the reflective surface.

A device for carrying out the method is also provided. The device includes a light source for directing a beam of light towards the reflective surface from which the beam of light is reflected. A first photodetector measures the intensity of the reflected beam of light at a first distance from the reflective surface. A photodetector, preferably a second photodetector, measures the intensity of the reflected beam at a second distance which is further from the reflective surface than the measurement made by the first photodetector. A readout system receives the measurements made by photodetectors and indicates the optical quality.

DETAILED DESCRIPTION OF THE INVENTION

Figure 1:
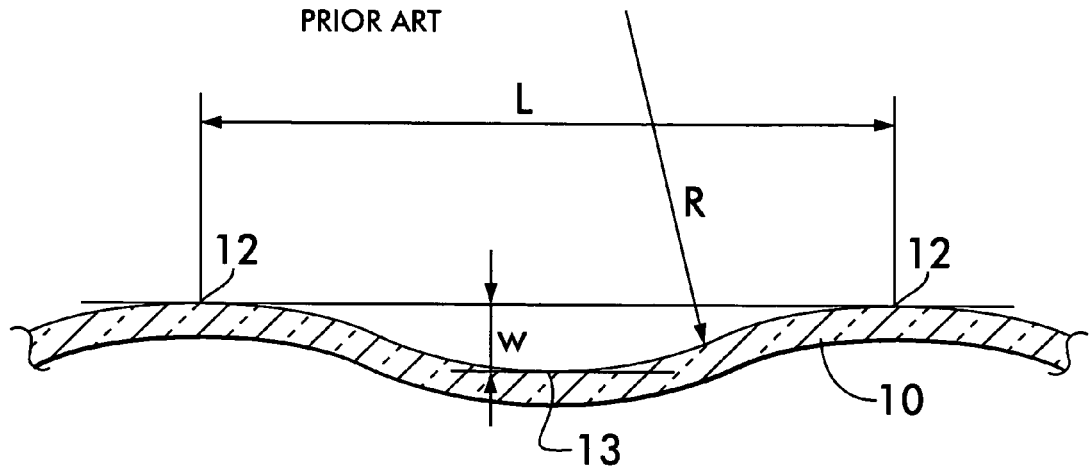
FIG. 1 is a schematic diagram showing roller-wave distortion.
Figure 1A:
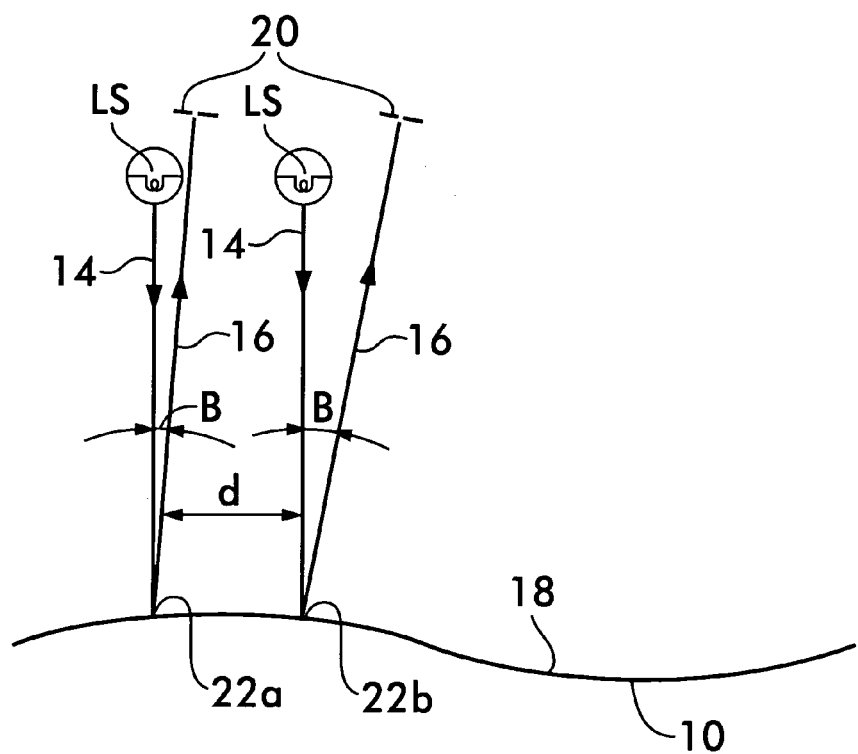
FIG. 1A is a schematic view of a known optical measuring method.
Figure 1B:
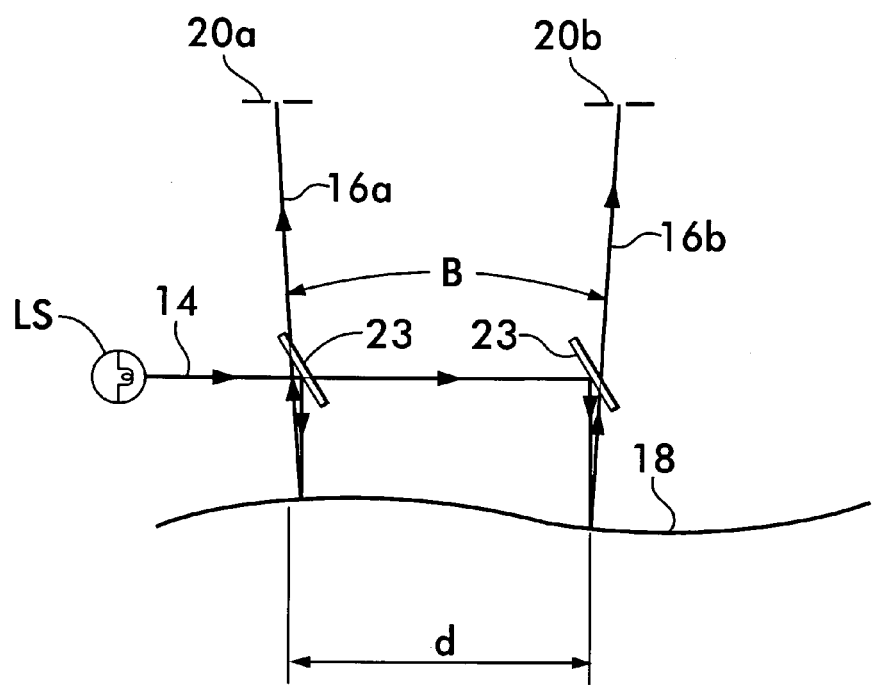
FIG. 1B is a schematic view of another known optical measuring method.

As discussed above and illustrated in FIG. 1, glass undergoing the heat-tempering process deforms out of its plane, forming a wavy pattern called "Roller Wave". The reference letters and definitions relevant to FIG. 1 are defined as follows:

L=wavelength
w=peak-to-valley depth
R=radius of curvature (Note: F=R/2)
D=Optical power (Note: D=1/F)

The peaks 12 and valleys 13 of the waviness are spaced by a distance L, called wavelength. Light reflection of the convex and concave regions introduce a distortion of reflected images, similar to the action of cylindrical mirrors. The image distortion depends on the local radius of curvature R and of the focal length F, related to R. Typically, a nearly perfect glass sheet has a radius of curvature larger than 100 meters, but a defective item could have locally a radius 10 meters or smaller. The optical effect of the local curvature is best described by the optical power D, related to the focal length and radius of curvature by:

$$D=1/F=2/R$$

The distortion introduced by a wavy surface can be evaluated quantitatively, measuring the optical power D. For example, measuring peak-to-valley depth w and the wavelength L yields the distortion, as shown in the Strainoptic Technologies Inc. Instruction Manual for Maintenance and Use of RWG Roller Wave Gage, and in the U.S. patents discussed above, and which describe the use of a reflected beam of light, or a pair of beams, with position-sensing detectors measuring the angular deviation of these beams. An equivalent result is obtained by the Schave reference, which described a device detecting the position of edges of a reflected beam.

The present invention eliminates the need for reflected beam position-sensing detectors as used in devices described above and provide means for measuring optical distortion more accurately. Instead, the reflected beam's divergence or convergence is measured directly, using the energy density principle, which is now described with reference to FIGS. 2A,2B,and 2C.

Figure 2A:
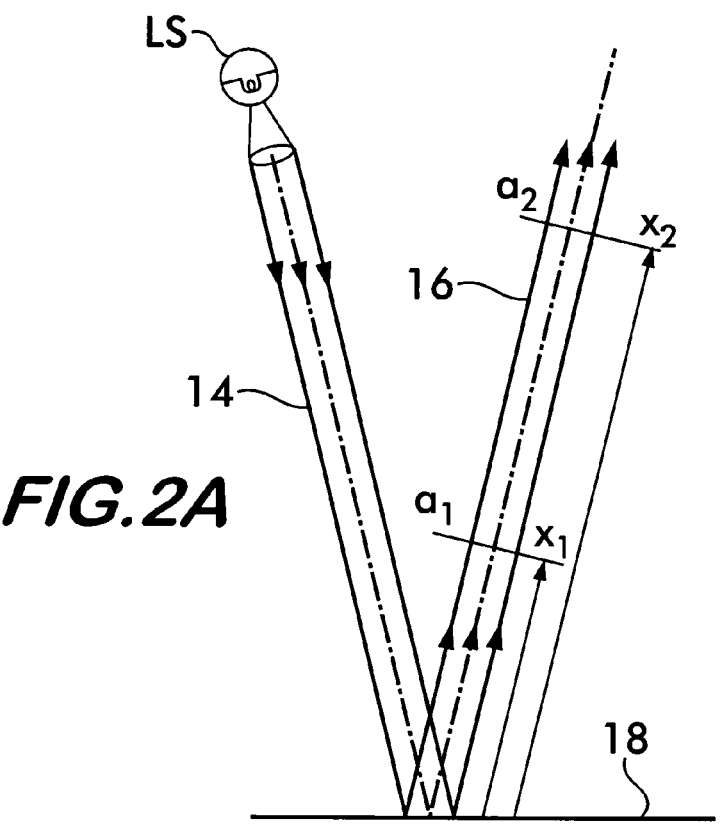
FIG. 2A is a schematic view of a reflection of light from a flat surface for purposes of demonstrating the principles of the invention.

As illustrated in FIG. 2A, when a cylindrical, collimated beam of light 14 from a collimated light source LS reflects off of a perfectly flat surface 18 the reflected beam 16 remains collimated, and neglecting light losses in the air, will illuminate a target placed in its way with the same luminous intensity, regardless of the target distance (e.g., $x_1$, and $x_2$) from the glass surface 18. Thus, with reference to FIG. 2A, the illumination at a target placed in the beam 16 at a distance $x_1$, will have the same illumination as at a target placed in the beam 16 at a distance $x_2$, or, put another way, the energy of the beam per unit area (the light intensity=I/a which can be expressed in units of watts/area) remains constant since target illumination is independent of the distance x from the surface 18.

Figure 2B:
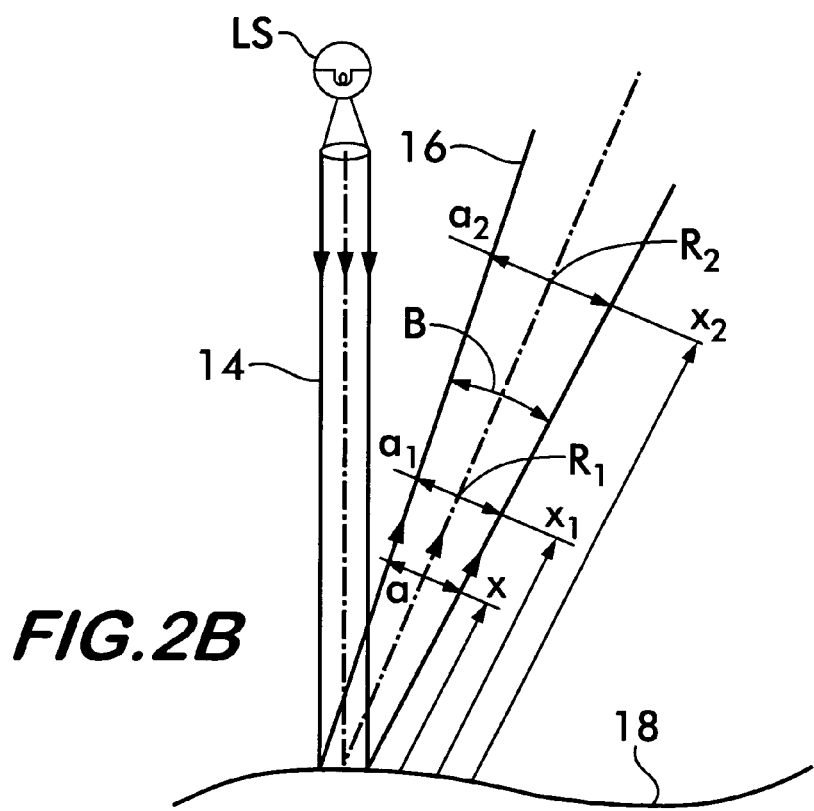
FIG. 2B is a schematic view of a reflection of light from a curved surface for purposes of demonstrating the principles of the invention.

With reference to FIG. 2B, as a result of surface waviness, the reflected beam 16 will acquire a diverging or converging angle B (diverging being illustrated in the FIG. 2B), covering an increasing or decreasing area a, as the distance x from the inspected surface 18 increases. Since the luminous energy I will be now spread over an increasing or decreasing area a, the light intensity (I/a) becomes a function of the distance x from the inspected surface 18, and also of the divergence angle B. Thus, with reference to FIG. 2B illustrating a diverging beam 16, the luminous energy at a distance $x_2$ is spread over an area $a_2$ that is larger than the area $a_1$, at $x_1$, where the luminous energy is spread over a smaller area. Measurement of the light intensity at two points $R_1$ and $R_2$, located at a distance $x_1$ and $x_2$ from the inspected surface 18, provides sufficient information to calculate the optical distortion. A sample calculation is illustrated with reference to FIG. 2C.

Figure 2C:
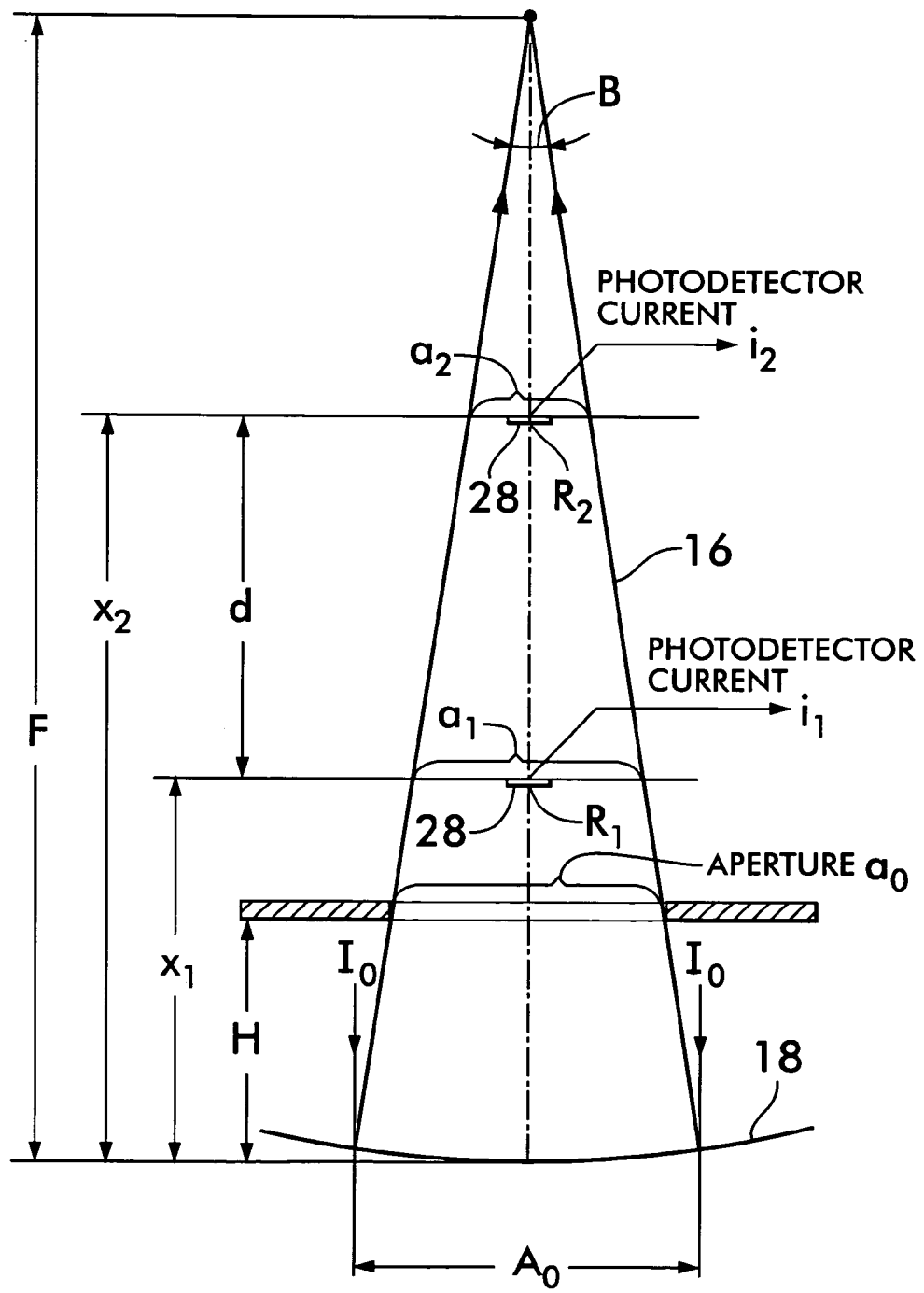
FIG. 2C is a schematic view of a reflection of light from a curved surface being measured for purposes of demonstrating the principles of the invention.

In FIG. 2C, a converging light beam 16 reflected from a cylindrical reflecting surface 18 is shown. The measuring of light intensity using a photodetector detector 28 is performed near the center of the reflected beam 16 at two points, $R_1$ and $R_2$, where the variation due to the vibration and to the motion of the measured item is minimized, making the measuring apparatus more accurate and reproducible than the beam position sensing devices. The term photodetector as used herein is any device capable of converting light intensity into an electric signal, and includes photo electric sensors, and photo diodes. As shown in the equations below, derived from the FIG. 2C, the optical distortion can be computed simply from the measured photoelectric currents $i_1$ and $i_2$ produced by the photoelectric detectors 28, $i_1$, and $i_2$ being the current produced by the photoelectric detectors 28 located in areas a, and $a_2$ respectively.

$$D = \frac{1}{F} = \frac{B}{A_o} \quad (1)$$

where $A_o$=the area of surface 18 being sampled (illuminated);

$$B = \frac{a_1 - a_2}{d} \quad (2)$$

where $a_1$, and $a_2$=the illuminated areas at R1 and R2 respectively, and B is the convergence angle;

Measured photoelectric currents $i_1$ and $i_2$ at points $R_1$ and $R_2$ respectively by the photodetectors 28 are proportional to the source intensity $I_0$:

$$i_1 = \frac{I_o}{a_1} \quad \& \quad i_2 = \frac{I_o}{a_2}$$

Change in the size of the illuminated areas is related to the change in measured intensities:

$$a_1 - a_2 = Z = I_o\left(\frac{1}{i_1} - \frac{1}{i_2}\right) \tag{3}$$

From the geometry it can also be shown that $$A_o = a_o + H \cdot B = a_o + \frac{H}{d}(a_1 - a_2) \tag{4}$$

where $a_0$ is the aperture of the measuring system and H is the distance of the aperture from the surface 18.

Combining eq. 1, 2, 3 & 4 yields:

$$D = \frac{a_1 - a_2}{a_o d + H(a_1 - a_2)} = \frac{Z}{a_o d + HZ} \tag{5}$$

For high-sensitivity of detection, H is small and d is large, making H/d negligible.

The above equation thus reduces to:

$$D = \frac{Z}{a_o d}$$

In essence, the new method permits measuring the optical distortion of a reflecting surface by simply measuring a differential output of two photodetectors.

Apparatus and Method for Measuring Optical Distortion

Figure 3:
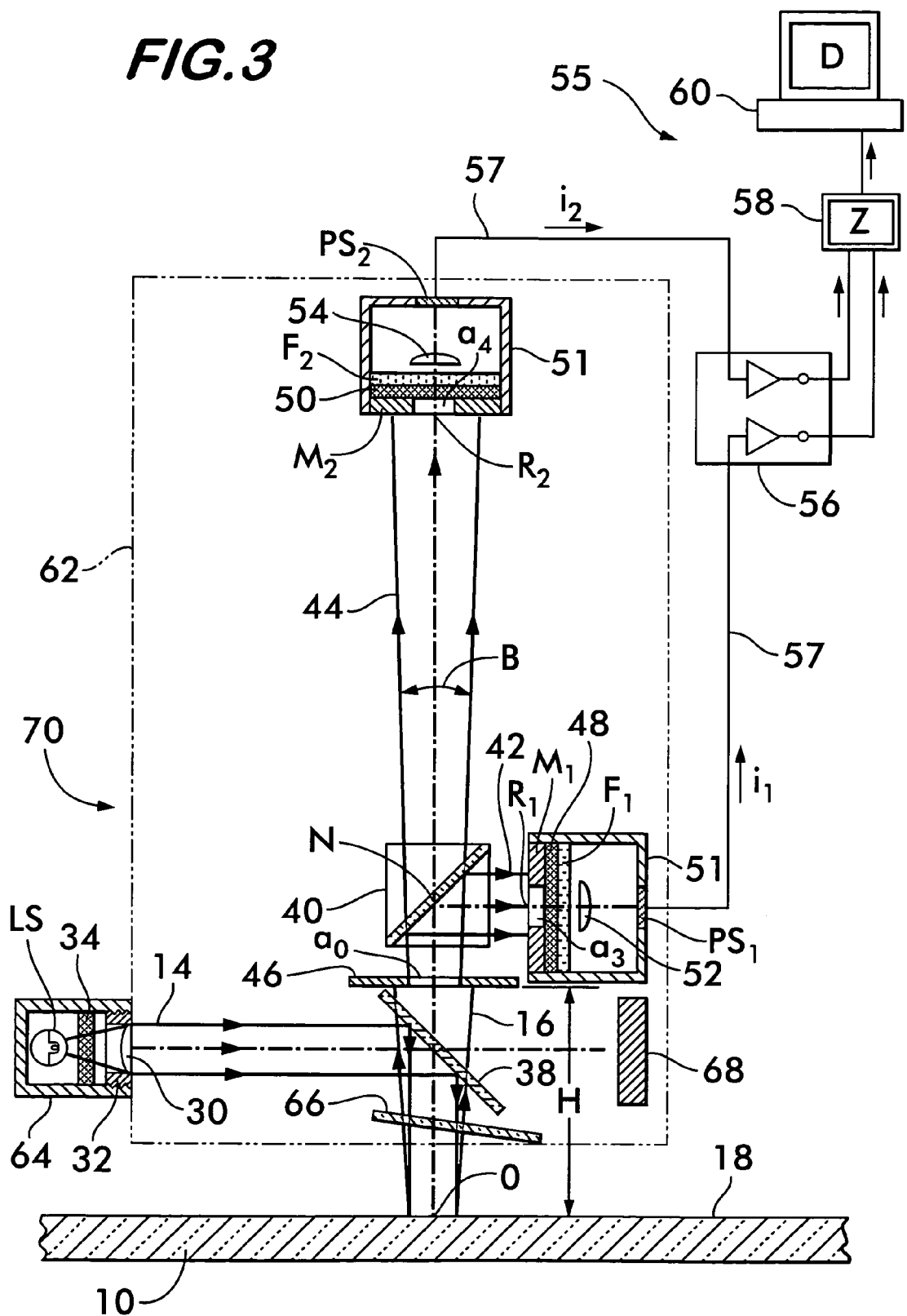
FIG. 3 is a schematic view of a preferred embodiment of the invention.
Figure 4:
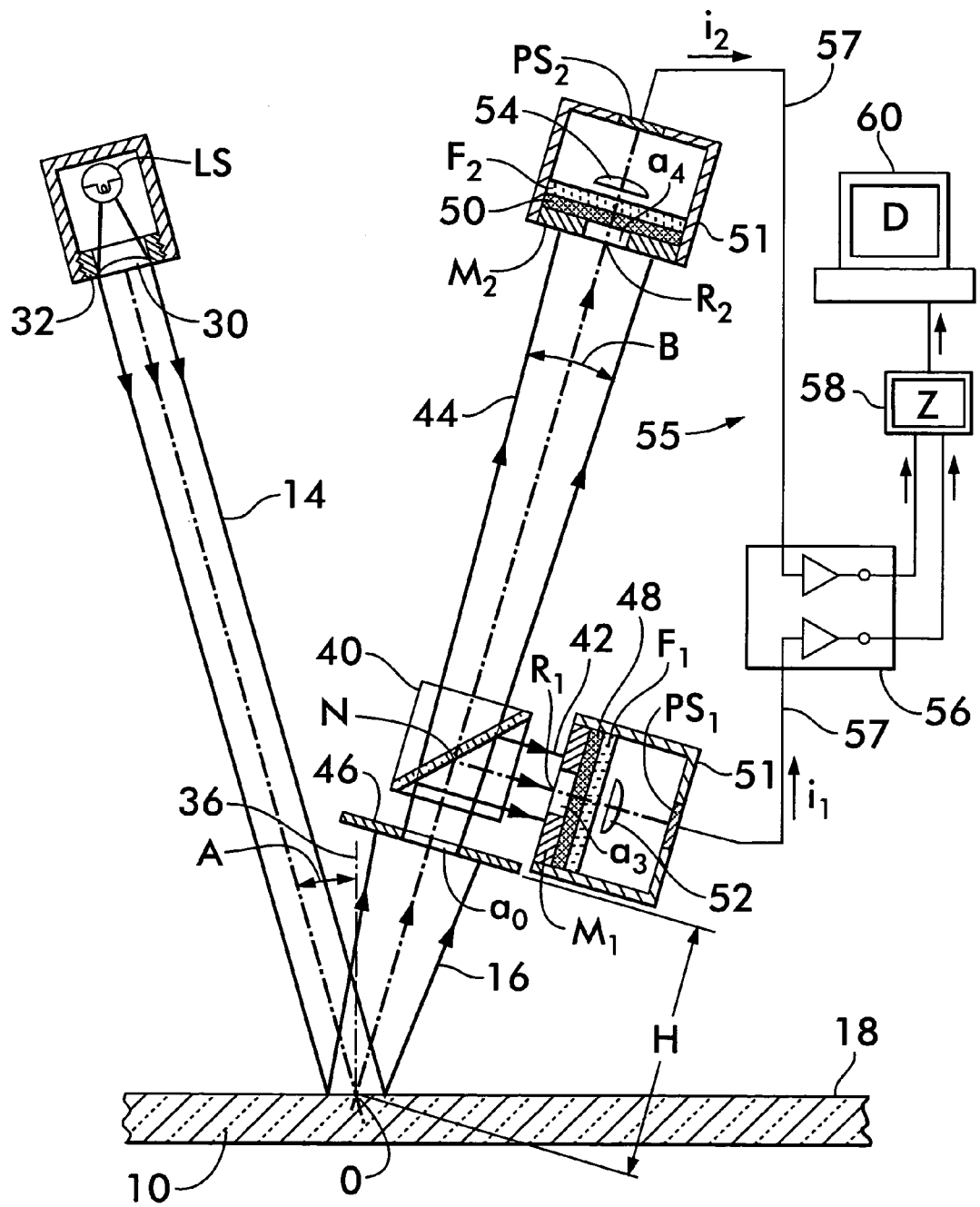
FIG. 4 is a schematic view of another preferred embodiment of the invention.

To better illustrate the principle of the new method and apparatus, reference is made to FIGS. 3 and 4. It is understood that these drawings are simplified, to better illustrate the methodology, and that any person skilled in the art can produce a large variety of optical element arrangements to accomplish essentially the same result.

Shown in FIG. 3 is a preferred embodiment having a light source LS such as an incandescent lamp, a laser beam, a tip of a fiber-optic cable channeling the luminous energy from a remote source, or other suitable source. An incandescent point source of about 20 watts is suitable. The light source is placed in a focal plane of a lens 30, directing a collimated beam 14 of light toward the inspected region (sample area) of the glass sheet 10. In practice, as result of the size of the light source, the illuminating beam 14 will be slightly divergent or convergent. A divergence adjustment is provided by a focusing device 32, such as an adjustable housing, adjusting the distance between the light source LS and the lens 30. A diffuser 34 can be provided between the light source LS and the lens 30. A diffused light source can provide equivalent results since the surface of the diffuser functions as an infinite number of point sources located in the same plane, each one behaving as a single point.

The incidence angle "A" (see FIG. 4) between the incident beam 14 and the normal 36 to the surface 18 of the glass 10 is preferably very small, as shown in the FIG. 3. To obtain a small angle A, a beam splitter 38 is mounted to receive the illuminator beam 14 and direct this beam in a direction towards the surface 18 and perpendicular to it. An alternative design, shown in FIG. 4, incorporating a large angle "A" is equally effective, and offers an equivalent solution. This configuration eliminates light losses due to the presence of the beam splitter 38.

The light beam 14 is then reflected from the surface 18, the reflected beam being illustrated with reference numeral 16. To permit measurement of the light intensity at two points $R_1$ and $R_2$, distant $x_1$ and $x_2$ respectively from the inspected surface 18, another beam splitter, or a beam-divider cube 40 (a 50—50 divider being preferred) intercepts the reflected beam 16, dividing the reflected beam into two beams 42 and 44 which reach the $R_1$ and $R_2$ points after traveling a distance $x_1$, and $x_2$ respectively, where $x_1$=ONR$_1$, and $x_2$=ONR$_2$, as shown in FIGS. 3 and 4 (the distance $x_1$, e.g., being the distance from point O to N to $R_1$). Since the sensitivity of detection is proportional to the distance d between the interception points $x_1$, and $x_2$ (see FIG. 2C), it is advantageous to make the distance d as large as practical. To measure distortion between 20 and 150 mdpt (millidiopters) typically encountered when inspecting tempered glass, a 50 mm diameter beam 14 can be used, with the distance d between the paths ONR1 and ONR2 about 400 mm. The distance ON should be kept as small as practical. It is understood by those in the art that the distances from the reflective surface 18 at which the light intensity measurements are made, e.g., $x_1$ and $x_2$, is the distance the light travels from the reflective surface 18 to $R_1$ and $R_2$, not necessarily the actual straight line distance from the reflective surface 18 to $R_1$ and $R_2$. For example, mirrors, in a manner known in the art, can be used to increase the distances $x_1$ and $x_2$ without increasing the actual distance of $R_1$ and $R_2$ from the surface 18. The distances $x_1$ and $x_2$ are the distances the light travels from the surface 18 to $R_1$ and $R_2$.

To measure the light intensity at $R_1$ and $R_2$, an aperture mask 46 having an opening of area $a_0$, may be incorporated, to control the size of the measured beam, admitting only the central region of the reflected beam 16 where the uniformity of the energy distribution is better. A mask 46 having an aperture $a_0$ slightly smaller than the original beam 14 is suitable.

Masks $M_1$ and $M_2$, having apertures $a_3$ and $a_4$ respectively, also permit selection of the portion of the beam used for the light intensity measurements, rejecting peripheral regions that are affected by the glass motion. Aperture $a_3$ is preferably smaller than $a_2$ since the light beam at the further pont $R_2$ is spread out more, a suitable $a_4$ being about 25 mm and a suitable $a_3$ being about the half that size. Color selective filters F1 and F2 can be used to select a suitable range of wavelengths, especially when coated glasses are inspected. Addition of diffusers 48 and 50 provide an integrating action, further eliminating an undesired sensitivity to small displacement of the beam center due to solid-body motion. Condenser lenses 52 and 54 can be incorporated to improve the light efficiency of these diffusers. The light intensity at $R_1$ and $R_2$, over the area ($a$, and $a_2$ in FIG. 2C) limited by the masks $M_1$ and $M_2$ is measured using suitable photodetectors $PS_1$, and $PS_2$, such as silicon photo diodes or any other suitable device. It is seen that each photodetector can be housed in an assembly 51 with the other related components, for example, photodetector $PS_1$ is in an assembly with Mask M1, filter F1, diffuser 48, and condenser 52.

A readout system 55 in communication with the photodetectors $PS_1$ and $PS_2$ through wires 57 is provided to analyze the measurements and display the results in a desired format. For example, the readout system 55 can include a photoelectric amplifier/readout instrument 5 whereby photoelectric currents $i_1$ and $i_2$, proportional to the light intensity at $R_1$ and $R_2$ are displayed by the photoelectric amplifier/readout instrument 56. In addition, the readout system 55 can include a differential amplifier 58, having an adjustable gain for calibration, which receives the output of the detectors $PS_1$ and PS2, measuring and displaying the difference Z between the light intensities $i_1$, at the point $R_1$ and $i_2$ at the point $R_2$. The analogue output of the photodetector/amplifier can be furthermore digitized, and connected to a computer 60 as part of the readout system, for data storage, graphic display of information and statistical presentation.

Using simple relations of geometrical optics, illustrated in FIG. 2C, the measured optical distortion D is related to the measured difference of light intensities Z, by the following equation:

$$D=Z/(H*Z+a_0*d)$$

Where H, $a_0$, and d are geometrical factors defined by distances $x_1$, $x_2$ and by the position of the instrument above the inspected surface, and H is shown in FIGS. 3 and 4. For small values of H, preferably about 50 mm, the above equation reduces to:

$$D=Z/(a_0*d)=K*Z$$

showing a direct proportionality between the optical distortion D and the measured output Z.

The device of the present invention should preferably be calibrated before use. For example, this can be done by using the device to measure a defect free flat piece of glass and adjusting the device so that the difference between the two currents $i_1$ and $i_2$ is zero to indicate an absence of optical distortion, e.g., adjusting the amplifier 56. The proportionality constant $K=1/a_0*d$ is measured in a calibration experiment, using a surface with a known radius of curvature, the device then being calibrated, for example, by adjusting the gain of the differential amplifier 58, or by a suitable software procedure for calibration.

The present invention also permits measurement of curvature in arbitrarily selected planes of the surface 18 being measured. This selection can be made using masks $M_1$ and $M_2$, shown in FIGS. 3 and 4, with a slit shaped aperture that permits sensing of light intensity variations due to divergence or convergence in a plane parallel to the slit only. For example, when sensing a cylindrical roller wave curvature, the sensitivity to the curvature in the plane perpendicular to the roller wave can be decreased or increased, depending on the test objectives, by placing the slit parallel to the direction of the rolls.

As shown in FIG. 3, the various components can be mounted within a housing 62 configured to minimize background light from entering the housing and interfering with the measurements. The light source LS can be mounted in an adjacent housing 64, such as an electrical box, mounted on the outside of the housing 62 to allow convenient access to the light source, such as a bulb, for easy changing without having to open up the main housing 62. An opening in the side of the housings 62 and 64 between the two allows the light to enter the main housing 62. A window 66, preferably of flat glass, allows the light beam 14 to leave the housing 62, reflect off surface 18, and reenter the housing 62 for measurement. The window 66 is preferably angled slightly as shown to eliminate undesirable reflections of light. Adjacent the beam splitter 38 is an anti-reflecting surface 68 to eliminate stray light that may pass through the beam splitter 38 from the light source LS.

Figure 5:
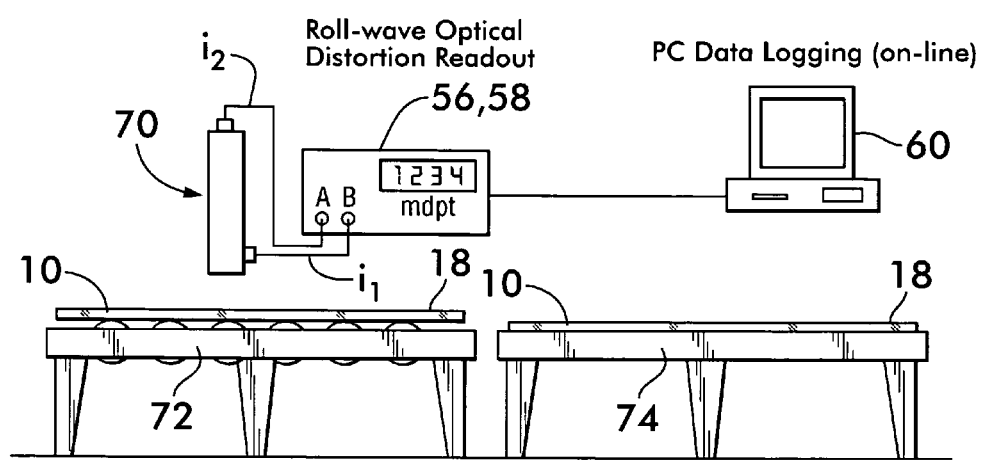
FIG. 5 is a schematic view illustrating the use of the present invention.

It is seen that the apparatuses of FIGS. 3 and 4 can inspect the optical quality or distortion of a reflective surface 18 at a single point or region of the sheet 10 (off-line), or can inspect a selected line along the sheet 10 as the sheet 10 is moved relative to the apparatus (on-line). For example, illustrated in FIG. 5 is an apparatus 70 similar to that described with reference to FIG. 3 positioned above a roller bed 72. The sheet 10 to be inspected moves on the roller bed 72 beneath the device 70 as the device 70 inspects the surface 18 along a line on the surface 18. Alternatively, the sheet 10 can be placed on a flat table 74 for inspection at specific points or regions on the surface 18.

While particular embodiments of the invention are described herein, it is not intended to limit the invention to such disclosure and changes and modifications may be incorporated and embodied within the scope of the appended claims.

What is claimed is:

1. A method for inspecting the optical quality of a reflective surface, said method comprising:
   (a) reflecting a beam of light off of the reflective surface;
   (b) measuring an intensity of said reflected light at a first distance from said reflective surface;
   (c) measuring an intensity of said reflected light at a second distance from said reflective surface, said first distance being different than said second distance; and
   (d) comparing the light intensity measured in paragraph b with the light intensity measured in paragraph c to determine the optical quality of the reflective surface.

2. The method of claim 1 wherein the beam of paragraph (a) is provided by an incandescent light source.

3. The method of claim 2 wherein the beam of paragraph (a) is provided by a collimated incandescent light source.

4. The method of claim 1 wherein the measuring functions of paragraphs (b) and (c) are carried out with a photodetector.

5. The method of claim 1 wherein the measuring functions of paragraphs (b) and (c) each comprise the step of generating an electric signal representative of the light intensity being measured.

6. The method of claim 5 wherein the step of generating an electric signal representative of the light intensity measured is carried out with at least one photodetector capable of producing an electric current proportional to the light intensity being measured.

7. The method of claim 4, further comprising the step of providing a mask having an aperture through which said light passes to said photodetector, said aperture having a geometry chosen to control a directional sensitivity of the optical quality being determined.

8. The method of claim 1 wherein step d includes the step of calculating the optical distortion.

9. The method of claim 1 further comprising the step of splitting the reflected light into at least two light beams, a first of said two light beams being measured in step b, a second of said two light beams being measured in step c.

10. The method of claim 9 wherein step b and step c are carried out at the same time.

11. A method for inspecting reflective surfaces that could contain a defective region where the surface is slightly curved, resulting in changes of reflected light direction and a distortion of reflected images, said method comprising:
(a) directing a beam of light towards the reflective surface;
(b) reflecting said beam of light off of the reflective surface;
(c) measuring an intensity of said reflected light at a first distance from said reflective surface;
(d) measuring an intensity of said reflected light at a second distance from said reflective surface, said second distance being further from said reflective surface than said first distance; and
(e) determining an optical quality of the reflective surface using the measurements of steps c and d.

12. The method of claim 11 wherein step e is carried by calculating the optical distortion using the measurements of steps c and d.

13. The method of claim 11 wherein steps c and d are carried by producing an electrical signal indicative of the light intensity.

14. A device for inspecting the optical quality of a reflective surface, said device comprising:
a light source for directing a beam of light towards the reflective surface such that said beam of light is reflected from said surface;
a first photodetector disposed for measuring the intensity of the reflected beam of light at a first distance from said reflective surface;
a second photodetector disposed for measuring the intensity of the reflected beam of light at a second distance which is further from said reflective surface than said first distance; and
a readout system in communication with said first and second photodetectors for indicating the optical quality of the reflective surface.

15. The device of claim 14 further comprising a beam splitter positioned to split the reflected beam into a first beam for measurement by said first photodetector, and a second beam for measurement by said second photodetector.

16. The device of claim 14 wherein said first photodetector is included in an assembly further comprising a mask having an aperture, a diffuser, and a condensing lens.

17. The device of claim 14 wherein said readout system comprises an amplifier for increasing the photodetector output.

18. The device of claim 14 wherein said light source comprises an incandescent bulb and a collimating lens.

19. The apparatus of claim 14 whereby the collimated beam illuminates the inspected surface at an angle other than normal.

20. The apparatus of claim 14, wherein said readout system includes a computer.

21. The apparatus of claim 14 further comprising a beam splitter positioned to direct the beam of light from the light source towards the reflective surface.

22. A method for inspecting the curvature of a reflective surface, said method comprising:
(a) reflecting a beam of light off of an area of the reflective surface;
(b) measuring an intensity of said reflected light beam at a first distance from said area and at a second distance from said area, said first distance being different than said second distance; and
(c) comparing the light intensity measured at said first and second distances to determine the curvature of the reflective surface, wherein a change in the light intensity between said first and second distances is indicative of the curvature.

* * * * *